United States Patent [19]

Sidman

[11] 4,450,150

[45] May 22, 1984

[54] BIODEGRADABLE, IMPLANTABLE DRUG DELIVERY DEPOTS, AND METHOD FOR PREPARING AND USING THE SAME

[75] Inventor: Kenneth R. Sidman, Wayland, Mass.

[73] Assignee: Arthur D. Little, Inc., Cambridge, Mass.

[21] Appl. No.: 262,149

[22] Filed: May 11, 1981

Related U.S. Application Data

[63] Continuation-in-part of Ser. No. 896,552, Apr. 14, 1978, abandoned, which is a continuation-in-part of Ser. No. 596,444, Jul. 16, 1975, which is a continuation-in-part of Ser. No. 361,182, May 17, 1983, abandoned.

[30] Foreign Application Priority Data

| | | | |
|---|---|---|---|
| May 10, 1974 | [CA] | Canada | 199552 |
| May 14, 1974 | [GB] | United Kingdom | 21361/74 |
| May 16, 1974 | [CH] | Switzerland | 6744/74 |
| May 17, 1974 | [DE] | Fed. Rep. of Germany | 2424169 |
| May 17, 1974 | [JP] | Japan | 48-54595 |
| Nov. 10, 1974 | [FR] | France | 74 34307 |

[51] Int. Cl.$^3$ ............ A61K 43/00; A61K 37/24; A61K 9/06
[52] U.S. Cl. ............ 424/1.1; 424/14; 424/15; 424/19; 252/62.53; 428/402.21; 604/891
[58] Field of Search ............ 128/260, 1.1; 424/15, 424/14, 1.1, 19; 252/62.53, 316

[56] References Cited

U.S. PATENT DOCUMENTS

| | | | |
|---|---|---|---|
| 4,230,685 | 10/1980 | Senyei et al. | 424/12 |
| 4,247,406 | 1/1981 | Widder et al. | 252/62.53 |
| 4,298,594 | 11/1981 | Sears et al. | 424/19 |
| 4,351,337 | 9/1982 | Sidman | 128/260 |
| 4,356,166 | 10/1982 | Peterson et al. | 424/19 |
| 4,357,259 | 11/1982 | Senyei et al. | 252/316 |

OTHER PUBLICATIONS

Sidman, K. R. et al., Naltrexone, Research Monograph 28, National Institute on Drug Abuse, (1980), pp. 214-232.

Sidman, K. R. et al., J. Membrane Science, vol. 7, (1980), pp. 277-291.

Sidman, K. R. et al., Biopolymers, vol. 22, (1983), pp. 547-556.

*Primary Examiner*—Benjamin R. Padgett
*Assistant Examiner*—M. Moskowitz
*Attorney, Agent, or Firm*—Richard J. Hammond

[57] ABSTRACT

An implantable drug deliver depot comprising a hydrophilic poly(glutamic acid-co-ethyl glutamate) structure having one or more substances, e.g., drugs and/or diagnostic agents physically contained therein. The drug or diagnostic agent is released by its permeation of and diffusion through the copolymer structure. The depot may be designed to release the substance or substances at predetermined rates and in predetermined sequence. The copolymer structure ultimately biodegrades to glutamic acid. Among the preferred configurations for the depots are rods and closed-end capsules.

28 Claims, 19 Drawing Figures

IN VITRO RELEASE FROM 22/78 GLUTAMIC ACID/
ETHYL GLUTAMATE COPOLYMER CAPSULES.

IN VIVO RELEASE FROM 22/78 GLUTAMIC ACID/
ETHYL GLUTAMATE COPOLYMER CAPSULES.

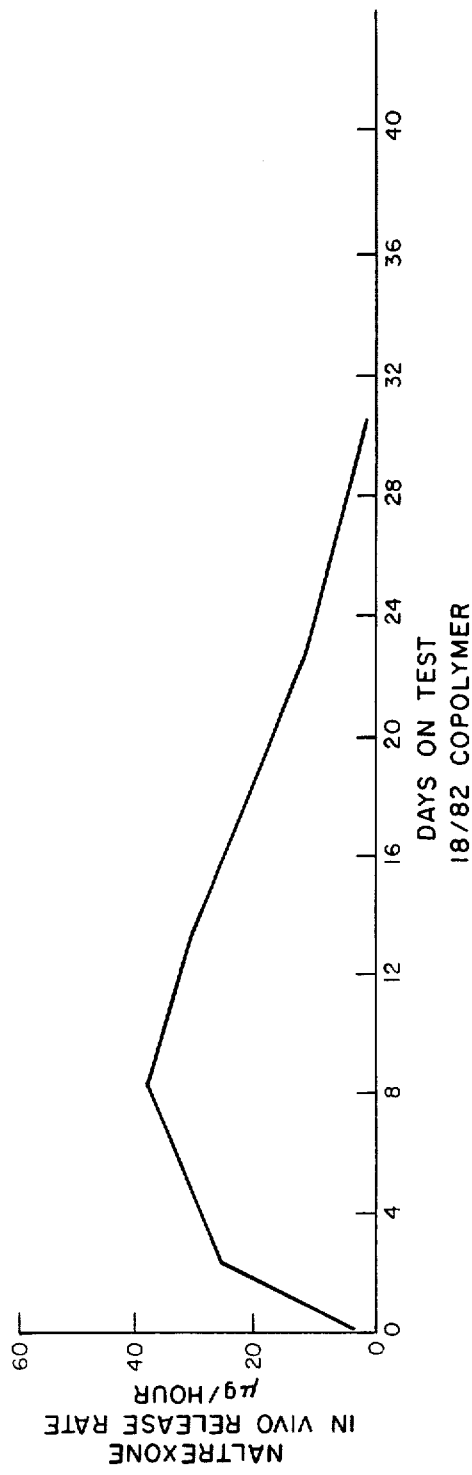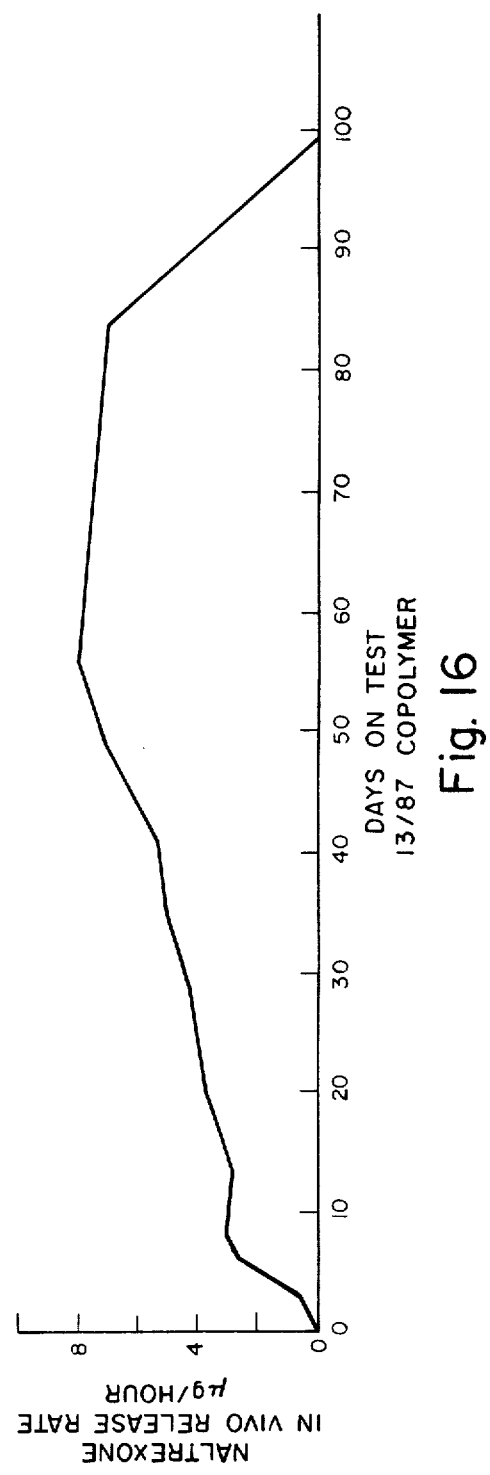

IN VIVO RELEASE FROM 22/78 GLUTAMIC ACID / ETHYL GLUTAMATE COPOLYMER RODS

BIODEGRADABLE, IMPLANTABLE DRUG DELIVERY DEPOTS, AND METHOD FOR PREPARING AND USING THE SAME

This application is a continuation-in-part of my application Ser. No. 896,552 filed Apr. 14, 1978 now abandoned, which was filed as a continuation-in-part of my application Ser. No. 596,444 filed July 16, 1975, which in turn is a continuation-in-part of my application Ser. No. 361,182 filed May 17, 1973, and now abandoned.

This invention relates to a new form of pharmaceutical preparation and more particularly to a biodegradable depot adapted to be located within a specified region or organ of the body of a living organism for releasing one or more substances (e.g., drugs or diagnostic agents) at a controlled rate for localized or systemic utilization.

BACKGROUND OF THE INVENTION

In the administration of drugs and in the diagnosis of certain pathological conditions it is highly desirable, if not necessary, to effect a controlled release of one or more substances within the living organism, in particular within a mammalian host. For example, the controlled release of drugs (a term used hereinafter to include all substances which effect some biological response) over a period of time within a specified region or organ of the body can be used as a continuous dose, long-term delivery system for such agents as antibiotics, cardioactive medicaments, narcotic antagonists, hypoglycemic agents, fertility control agents, and the like. Likewise, the implantation of a diagnostic substance such as a dye can be used to monitor the presence or absence of a pathological condition. Devices for administering such a controlled release of drugs are generally referred to as "depots" or "implants," the former term being used throughout the following description and claims.

FIELD OF THE INVENTION

Continuous, long term drug delivery devices have distinct advantages over oral administration or direct injection of drugs since neither of these earlier developed modes can achieve a desired blood level of a drug in circulation for an extended period of time. Oral administration or direct injection bring about a pulse entry of the drug which may create drug concentrations beyond the capacity of the active centers to accept the drug, and may also exceed the capacity of the metabolic and excretory mechanism of the living organism. Thus, if the level of the drug remains elevated, tissues and/or organs may sustain detrimental effects. One technique for reducing excessive concentrations has been to modify the drug structure to provide a longer metabolic half-life; but this in turn has frequently demonstrated lowered therapeutic effectiveness.

To avoid the disadvantages of oral or direct injection administration of drugs, a number of modes of administration of continuous dose, long-term delivery devices have been used or proposed. These include devices based upon ingestion, injection, vaginal and uterine insertion, percutaneous application (see for example U.S. Pat. Nos. 3,598,122 and 3,598,123) and subcutaneous implantation. While all of these routes of administration may be found useful under one set of circumstances or the other, the use of subcutaneous implants offers a particularly desirable combination of properties to permit the administration of substances on a localized or systemic basis. To this end, subcutaneous implants serving as depots capable of slow release of a drug have been proposed. These implants suggest the possibility of attaining continuous administration over a prolonged period of time to achieve a relatively uniform delivery rate and, if desired, a static blood level. Since an excessive concentration of drug never enters the body fluids, problems of pulse entry are overcome and metabolic half-life is not a factor of controlling importance.

Despite the advantages of administering drugs from implants, prior art devices designed for this purpose have possessed one or more disadvantages which limit their acceptability and efficacy. Among such disadvantages are nonbiodegradability which may require a surgical procedure to remove them; nonbiocompatibility which may result in the introduction of undesirable and even harmful substances into the body; antigenicity which gives rise to the production of unwanted antigen bodies in the system; and difficulty in controlling release rates of the drugs.

DESCRIPTION OF THE PRIOR ART

In the prior art, a number of matrix materials and several different structural designs have been proposed for subcutaneous implants. Such materials as hydrogels, gelatin, carboxymethyl cellulose, organopolysiloxane rubbers, polyurethanes, waxes, polyvinyl alcohol, polyglycolic acid, and polylactic acid have been suggested for this purpose.

Organopolysiloxane rubbers as carriers for the controlled release of drugs have received widespread attention. The use of such materials in implant devices is described in U.S. Pat. Nos. 3,279,996 and 3,518,340. Implants which use any of these materials as substrates or carriers which are not absorable by the living organism into which they are introduced normally require removal by surgery. The silicone rubbers are among the nonabsorbable materials and therefore they suffer from this drawback. Typically, implants formed of silicone rubber, or of any of the other above-named materials, have been fabricated either in the form of closed hollow tubes or capsules (with or without a sponge sleeve) in which the drug is contained for diffusion through the tube walls; or they have been made up into structures of homogeneous polymer-drug blends. Another type of subcutaneous implant which requires removal is described in U.S. Pat. No. 2,625,158.

Those matrix materials, such as carboxymethyl cellulose and polyvinyl alcohol, which are water-soluble are unsatisfactory because it is not possible to control the drug release rate from them over any appreciable length of time. Those matrix materials, such as hydrogels, gelatin and collagens, which are water-swellable provide inherently rapid drug release because of their inability to retain the drug in a swelled condition. Moreover, a material such as gelatin has an extremely complex chemical structure formed of some twenty amino acids and there appears to be no satisfactory way to control or adjust its physical properties for use as an implant matrix. Collagen-based implants are described in the literature (see for example Rubin et al "Collagen as a Vehicle for Drug Delivery", *The Journal of Clinical Pharmacology*, August-September, 1973, pp. 309–312.)

More recently, absorbable, biocompatible matrix materials formed of polyglycolic acids, polylactic acids or mixtures of these have been disclosed. (See for example U.S. Pat. No. 3,773,919 and reports on Contract DADA-17-72-C-2079 to Dynatech Research and Development Co., with U.S. Army Medical Research and Development Command, Washington D.C. (1972).) These delivery devices consist of a polymer matrix in which the drug is physically entrapped. The drug is released, not by diffusing through a polymeric membrane, but by hydrolytic breakdown of the polymer matrix itself. As the polymeric matrix disintegrates, the enclosed drug is released into the surrounding body fluids. By the time all of the drug has been released from the matrix, the polymer fragments have been almost completely absorbed. Although these matrix materials make it possible to provide biodegradable and biocompatible implant devices having less rapid release rates, they present serious problems in the accurate control of release rates. These problems in release rate control arise because the polylactic acids and polyglycolic acids in degradation break down to form lactic acid and glycolic acid. Degradation is the result of hydrolysis which is dependent upon both pH and degree of crystallinity of the polymers. Since the products of these hydrolysis reactions are acids, there is a tendency for the products that do not immediately diffuse away from the implant site to accelerate further hydrolysis. In addition, the crystalline regions degrade at a much slower rate than the amorphorus regions, thus giving rise to a nonuniform degradation pattern and a porous structure from which the drugs may be released at an uncontrollable rate.

More recent prior art discloses an ocular or implant device formed of a hydrophobic polycarboxylic acid (partially esterified if required) having an average of one carboxylic hydrogen for each 8 to 22 total carbon atoms as a matrix material (U.S. Pat. Nos. 3,811,444 and 4,014,987) and an ocular or implant device formed of ethylene-vinyl acetate copolymer as the matrix material (U.S. Pat. No. 4,052,505).

In a copending application Ser. No. 596,444 filed July 16, 1975, I have disclosed an implant device designed for the controllable release of a substance into a living organism, and particularly into a mammalian host, comprising a biocompatible, biodegradable poly-α-amino acid structure containing the substance to be released. Release of the substance may be through diffusion, hydrolysis of the polymer or a combination of both of these mechanisms. The poly-α-amino acid, which is a synthetic polymer composed of α-amino acid residues linked by peptide bonds, is degradable through the action of one or more enzymes which are provided by the body fluid, tissue or organ of the host within the area of the implant. The degradation products, i.e., amino acids, are metabolized or excreted by the organism during and/or after release of the substance. The implant may be in the form of a film, rod, fiber, hollow cylinder, closed tube, microcapsule, microchip, and the like; and it may have the drug so distributed as to provide a constant or a changing rate of release. The poly-α-amino acid may be a homopolymer or a copolymer of two or more amino acids; and it may be chosen as to be biodegradable through action of one or more enzymes which are normally present in the living organism or through action of one or more enzymes developed by a pathological condition thus effecting the triggering of the release only upon certain predetermined conditions.

These implants based upon the use of homopolymers or copolymers of amino acids exhibit relatively slow degradation rates, a fact which may detract from their use in delivering certain drugs.

Some work has been reported on implants formed by chemically bonding drugs to polypeptides (see for example Jablon, P. A. M., Ph.D. Thesis, Purdue University, 1969). This approach necessitates providing a drug having a reactive site amenable to chemical bonding to the polypeptide; and it also introduces the danger that in the breaking of the chemical bond to release the drug the effectiveness and acceptability of the drug to the system may be materially altered. Moreover, the drug-polypeptide complex will, in fact, represent a new drug of unknown properties. Finally, an implant in which the drug is chemically bonded to the matrix material can not release the drug from the matrix by the process of diffusion, since release is predicated on the actual breaking of chemical bonds.

U.S. Pat. No. 3,493,652 teaches the incorporation of medicaments such as cardioactive, adrenergic, cholinergic, antispasmodic and curariform agents, tranquilizers, antihistamines, antibiotics and the like into a matrix which contains one or more enzymes or enzyme precursors capable of digesting the matrix material which, in turn, may be formed of such diverse materials as casein, fibrinogen, proteins, polypeptides with free amino groups, urea and amino acids. The dosage formulation may take many different forms including suspensions, emulsions, tablets (sublingual, buccal, oral or vaginal), capsules, ointments, suppositories and implants. When such a controlled release medicament is introduced into a living organism it must, of necessity, introduce both the substrate material and enzyme into the system and one or both of these may be antagonistic to the system. In particular, to introduce those enzymes which are not normally present in the living organism may result in harmful side effects. Moreover, enzymes are known to degrade or denature and this process may take place prior or subsequent to the administration of the dosage. In the first case, the effectiveness of the dosage-contained enzyme is lessened or even cancelled; and in the second case, premature enzyme degradation could materially alter or even destroy any control over the drug release rate.

A field which is somewhat related to implants is that concerned with sutures. Prior art in this field teaches, among many variations, the incorporation of antiseptics into sutures derived from animal tissue (U.S. Pat. Nos. 923,768 and 1,382,715); sutures of proteins or other nitrogenous amphoteric organic materials having a germacide chemically bonded thereto (U.S. Pat. No. 3,642,003); and sutures formed of or incorporating polymers and/or copolymers of glycolic acid and lactic acid (U.S. Pat. Nos. 3,636,956 and 3,736,646). Finally, the prior art discloses biodegradable sutures formed of a copolymer of glycolic and lactic acids (U.S. Pat. No. 3,736,646) and of a polylactide polymer or copolymer (U.S. Pat. No. 3,636,956).

Inasmuch as the matrix materials of the implant depots of this invention are copolymers of an amino acid, and an amino acid ester, the prior art disclosing the use of polypeptides in therapeutic devices also deserves attention. Such prior art includes sutures made of copolypeptides (U.S. Pat. No. 3,371,069); highly permeable films for internal and external dressings and dialysis membranes (Japanese Kokai No. 48-961); wound dressings formed of a polypeptide film containing a therapeutic agent and a carrier which transports the therapeutic agent to the dressing surface (U.S. Pat. No. 3,867,520) and dressings for burn wounds formed of a nylon velour fabric laminated with a synthetic polypeptide material designed to cover burns to provide a framework into which fibroblastic proliferation could occur (Spira et al "Evaluation of Synthetic Fabrics as Artificial Skin Grafts to Experimental Burn Wounds" *J. Biomed, Mater. Res.*, 3: 213-234 (1969) and Walder et al "Evaluation of Synthetic Films as Wound Covers" *Trans. Amer. Soc. Artif. Int. Organs*, 15: 29-32 (1969).)

It will thus be apparent from this discussion of the prior art that implants for controlled drug release have distinct theoretical advantages; but that there is a need for an improved implant device to achieve a continuous dose, controlled release of drugs or other substances which overcome the major disadvantages (i.e., difficulty in continuously controlling the release of the drugs, production of unwanted degradation products, slow rate of matrix degradation and/or the need for surgically removing the implanted matrix) associated with the presently available implant devices.

It is therefore a primary object of this invention to provide an improved drug depot for achieving continuous-dose, controlled-release of drugs or other substances such as diagnostic agents. It is a further object of this invention to provide a drug depot of the character described which is biocompatible and biodegradable within a specified or predetermined period of time and which therefore eliminates the need of surgical procedures to remove a depot structure. An additional object of this invention is to provide an improved drug depot which exhibits improved release rate control, the rate of release being optionally constant or at some predetermined changing rate, and which is nontoxic, nonantigenic and noncarcinogenic. Another object is to provide a drug depot which is susceptible to practical synthesis and fabrication procedures and which is able to withstand sterilizing. It is yet a further object of this invention to provide an improved drug depot which may be used to deliver a wide range of drugs or other agents which may be water-soluble or which may exhibit water-solubility in the low solubility range, i.e., 1-10 ppm., including two or more drugs simultaneously or serially.

It is another primary object of this invention to provide a method for forming biodegradable drug depots in various configurations to attain controlled drug release at a constant or varying release rate and to attain the release of two or more drugs either simultaneously or serially. Another object of this invention is to provide a process of the character described which is amenable to the formation of a drug depot to deliver a wide range of drugs and other substances such as diagnostic agents.

Still another primary object of this invention is to provide an improved method for the continuous, rate-controlled delivery of drugs and/or other substances into selected areas or organs of living organisms in a manner to minimize or eliminate the introduction of any substance, other than the drug or other agent, not normally present in the organism.

Other objects of the invention will in part be obvious and will in part be apparent hereinafter.

According to one aspect of this invention there is provided a depot suitable for implanting within a living host for the controllable release of at least one substance within the host, comprising a structure formed of a poly(glutamic acid-co-ethyl glutamate), which is hydrophilic and of uniform composition throughout, containing the substance in releasable form. Although the copolymer structure may take a number of different forms, solid rods and capsules are preferred.

According to another aspect of this invention there is provided a method for delivering at least one substance at a controllable release rate into a living host, comprising implanting into the host a depot containing a pharmaceutically effective quantity of the substance in releasable form, the depot, comprising a structure formed of a poly(glutamic acid-co-ethyl glutamate) which is hydrophilic and of uniform composition throughout.

According to yet another aspect of this invention there is provided, in conjunction with the manufacture of the depots, techniques for improving the performance of the depots. One of these techniques comprises treating the surface of the depot to minimize the initial burst of drug release normally encountered shortly after implanting the depot. Another of these techniques comprises introducing a suspending agent within a capsule depot, to ensure effective contact between the drug and casing wall to avoid a delay in drug release after implantation.

The invention accordingly comprises the several steps and the relation of one or more of such steps with respect to each of the others, and the article possessing the features, properties and the relation of elements, which are exemplified in the following detailed disclosure, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which

FIG. 15 is a plot of the in vivo release of naltrexone from 18/82 glutamic acid/ethyl glutamate copolymer capsules as a function of time;

FIG. 16 is a plot of the in vivo release of naltrexone from 13/87 glutamic acid/ethyl glutamate copolymer capsules as a function of time;

DETAILED DESCRIPTION OF THE INVENTION

Figure 1:
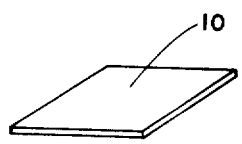
FIG. 1 illustrates an essentially "two-dimensional" implant device particularly suitable for in vivo testing.
Figure 2:
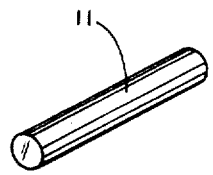
FIG. 2 illustrates a drug depot constructed in accordance with this invention in the form of a rod.
Figure 3:
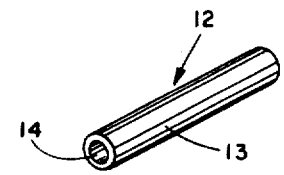
FIG. 3 illustrates a drug depot in the form of a hollow cylinder.

The biocompatible, biodegradable drug of this invention is formed as a structure in which the drug or other releasable substance to be delivered is physically contained in a copolymer of glutamic acid and ethyl glutamate, i.e., poly(glutamic acid-co-ethyl glutamate) structure. In the following description and claims the term "drug" is used in its broadest sense and it includes any substance which has any biological activity, whether such activity is medicinal or otherwise. For convenience in presenting this detailed description, the depot will be described in terms of containing a drug, although it is to be understood that it may also contain a diagnostic agent such as a releasable dye which has no biological activity per se. Thus, in its broadest sense, the implant may be defined as containing a releasable substance, which may or may not exhibit biological activity.

The polymeric structure, in which the drug is contained for release, is a copolymer of glutamic acid and its ethyl ester. This copolymer is represented by the following structure:

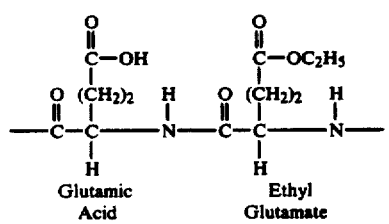

The homopolymer polyethyl glutamate, in contrast to the copolymer used in this invention, exhibits a degradation rate which is so slow as to make it essentially impractical as a depot structure. However, when a copolymer is formed with glutamic acid, the rate of biodegradation is materially increased, even with as little as five mole percent of glutamic acid. It appears that this small amount of the acid form may initiate a self-sustaining, self-catalyzing degradation process. On the other hand, copolymers with more than about 50 mole percent of glutamic acid render the depot structure so soluble in the internal host environment that biodegradation is too rapid to achieve a practical degree of control over the release of the drug carried in the depot. Therefore, in the poly(glutamic acid-co-ethyl glutamate) depot structure, the mole percent of glutamic acid present ranges between about 5 and about 50.

In order to achieve a predetermined essentially continuous controlled rate of drug delivery, the poly(glutamic acid-co-ethyl glutamate) used as the depot matrix material must be hydrophilic while remaining essentially water-insoluble. To meet this requirement of hydrophilicity the copolymer must be capable of absorbing at least 15%, and preferably 50%, of its weight in moisture in 48 hours when immersed in buffered physiological saline solution at 37° C. This degree of hydrophilicity permits the degradation of the matrix material to take place primarily through hydrolysis and results in its ability to gradually change chemical composition while at the same time retaining its basic configuration. Thus there is brought about the desired essentially continuous controlled drug release, whether the drug is soluble or insoluble in water, followed by the required biodegradation of the copolymer matrix after the drug has been released. It appears that the glutamic acid/ethyl glutamate copolymers degrade by a process that involves hydrolysis of the ethyl ester to produce a water-soluble copolymer. Subsequent hydrolysis of the peptide bonds produces glutamic acid. The glutamic acid then enters the metabolic pool to be incorporated into protein or expired as carbon dioxide, thus disposing of the copolymer after it has served its purpose. By proper initial choice of glutamic acid/ethyl glutamate ratios, the copolymer degradation rate may be adjusted and predetermined to run from several weeks to a year or longer.

The copolymer used in the drug depots of this invention are essentially uniform in hydrophilicity and in composition throughout anyone matrix component of the depot, e.g., throughout the walls forming a sealed capsule or throughout any layer of a rod.

As will be described below, a sealed capsule containing essentially pure drug is a preferred form of depot for water-soluble drugs. The use of hydrophilic copolymer of glutamic acid and ethyl glutamate makes it possible to construct such capsules to have the desired continuous, controlled drug release rates.

The prior art (U.S. Pat. Nos. 3,811,444 and 4,014,987) teaches the use of a hydrophobic poly(carboxylic acid), defined as one which absorbs not more than 10% of its dry weight, as an erodible release agent, the erosion being attained by hydrogen ionization. The drug contained in these prior art erodible drug depots is released as the surface of the depot is gradually sluffed off and the depot continually dissolves and gets smaller, whereas the drug contained in the drug depots of this invention premeates through a copolymer matrix which essentially maintains its structural integrity while changing chemical composition, presents a continually decreasing surface area with attendant decrease in the drug release rate; and, even more important, it essentially rules out the use of capsule-form depots.

As will be discussed in detail hereinafter, the copolymers used in forming the drug depots of this invention may be formed by copolymerizing benzyl glutamate and ethyl glutamate and then debenzylating the resulting copolymer. Variations in the permeability and in the rate of biodegradability of the copolymer may be attained for any glutamic acid/ethyl glutamate copolymer by the manner in which de-esterification is carried out, that is the extent to which the glutamic acid constituent of the copolymer is formed by de-ethylating a small amount of the ethyl glutamate constituent.

The biodegradable depot of this invention may be formed by one of several different techniques. If the implant comprises a matrix structure in which the drug to be released is distributed throughout in the desired concentration, it is preferred to physically incorporate the substance into the copolymer matrix and then shape the implant structure by casting from a solution, by injection molding, by extruding or by other suitable processes. If the depot takes the form of a capsule, the outside of which is formed of the copolymer without any drug, then a drug-containing core may be formed and coated with the copolymer or a drug core may be inserted into a tube and ends sealed thereon. Likewise, microcapsules and chips may be formed by well-known coating or microencapsulation techniques.

The implant is introduced within the living organism by any suitable technique, e.g., by a depot implantor.

The copolymers used in the formation of the depots of this invention must have sufficient mechanical strength to be formed into such configurations as tubes, rods, capsules, hollow cylinders, microcapsules, microchips, and the like. It should be noted that the depots of this invention are not desirably in the form of films or sutures and such are not contemplated as sufficient drug releasing shapes. The copolymers must also be of a type which lend themselves to formation into such structures by known fabrication techniques as described below.

The glutamic acid/ethyl glutamate copolymers are biocompatible and biodegradable. In being biocompatible, the polymers are nontoxic, nonantigenic and noncarcinogenic. In being biodegradable, they are capable of breaking down to form amino acids or related materials which can be assimilated within the host environment. As will be apparent hereinafter, the rate of biodegradation may be predetermined and controlled by such factors as copolymer composition and copolymer synthesis; and the optimum time of biodegradation will be chosen to be compatible with the frequency at which the depot must be implanted to attain the drug delivery level desired.

A wide range of drugs may be incorporated into these synthetic polymer matrices to form the implant devices of this invention. Such drugs include, but are not limited to, fertility control agents such as progesterone, d,l-norgestrel, levonorgestrel, norethindrone, estradiol valerate, medroxyprogesterone acetate, and hydroxyprogesterone caproate; narcotic antagonists such as naltrexone, naloxone and diprenorphine; anticoagulants such as heparin or ethylenediaminetetraacetic acid; antibacterials; antibotics; antineoplastic agents; cardiovascular agents such as digitalis, quinidine and nitroglycerine; immunological agents; central nervous system stimulants and depressants; antidiabetic agents, growth hormones, and the like. Diagnostic agents such as dyes (e.g., bromsulphalein) may be incorporated for implantation at a site where enzymes, formed as a result of a pathological condition to be detected, are available for the hydrolysis of the matrix material. The release of such diagnostic agents brought about by the presence of the pathologically-induced enzyme may be detected in the body fluids, e.g., the urine, to indicate the presence of the pathological condition being monitored.

The quantity of the drug or drugs or of diagnostic agent incorporated into the copolymer structure will depend upon the structural configuration of the depot, and the rate and the length of time over which it is to be released, which in turn will depend upon the permeability of the copolymer and the diffusion rate of the drug. In the case of rods or tubes where the drug is mixed throughout the copolymer matrix, the copolymer must be present in an amount sufficient to form an essentially continuous phase or network. This in turn dictates that the drug content of the depot be no more than about 70% by weight to insure the structural integrity of the device. In the case of capsules, and particularly where the copolymer is used only to form the capsule walls, drug contents as high as 90% to 98% by weight may be used.

As previously noted, the drug depot of this invention may take one of several forms. In those forms where the drug to be delivered is distributed throughout the copolymer serving as a matrix structure, the drug (or diagnostic agent) is blended with the polymeric matrix material and then the resulting physical mixture is fabricated into the desired structural shape.

Such blending may be done by one of several techniques. The first of these comprises forming a solution of the polymeric matrix material and adding the drug to the solution. If the solvent or solvent mixture used to form the solution of the matrix is also a solvent for the drug, then a homogeneous solution may be formed. If the solvent system is not a solvent for the drug, then the drug may be dispersed as fine particulate material, as a liquid, or in other suitable form, throughout the copolymer solution using, if necessary, a high-shear mixer to obtain a homogeneous suspension. The solution or suspension thus formed may be cast into ribbons such as illustrated in FIG. 1 which illustrates a depot 10. Solvent and casting conditions are chosen to prevent any appreciable segregation of the drug and polymer when the solvent is removed. The flat depot 10 of FIG. 1 exhibits a relatively constant surface area over its useful life within a living organism and hence it may be used to administer a relatively constant dose rate. The ribbon form of depot is not however, particularly amenable to administration by trocar, a fact which means that surgical implantation procedures may be required. This form of implant has, however, been found convenient for making in vivo and in vitro evaluations of a large number of drugpolymer combinations and it serves well as a model delivery system for such evaluation work.

Another blending technique may comprise mixing the drug with the dry copolymer matrix material in powdered form and then forming the desired structural shape with heat and pressure, the fabrication conditions being such as not to destroy the efficacy of the drug or to degrade the matrix material. The blend of drug and dry copolymer matrix material may be injection molded, compression molded or extruded into three-dimensional shapes of a required design.

Under some circumstances it may be necessary or desirable to add a processing aid in forming three-dimensional depot configurations such as illustrated in FIGS. 2–7.

A cylindrical shape represents one preferred configuration of the drug depot of this invention since it is possible to administer such devices by means of a trocar. Such a cylindrical shape may be in the form of a solid rod, a tube, or a capsule as shown in FIGS. 1–7. The depot 11 of FIG. 2 comprises a solid rod of the poly(glutamic acid-co-ethyl glutamate) having the drug distributed essentially uniformly therethrough; and the depot 12 of FIG. 3 comprises an open tubing having an external surface 13 and axial opening defining an internal surface 14. The combination of external surface 13 and internal surface 14 will increase the rate of drug release.

Figure 4:
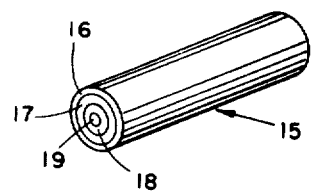
FIG. 4 illustrates a drug depot in the form of a layered rod in which the drug concentration is different from its adjacent layer or layers to achieve a predetermined rate of drug release.
Figure 5:
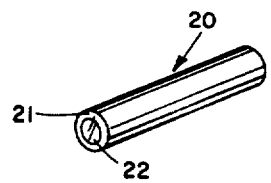
FIG. 5 illustrates a drug depot in the form of a rod with a core containing a drug different from the surrounding layer.

In the modification of FIG. 4, the cylindrically-shaped depot 15 is formed of multiple layers as exemplified by layers 16, 17, 18 and 19, the last serving as a core. In this depot embodiment, each layer may have a drug concentration different from that of an adjacent layer or layers. If these drug concentrations are arranged to provide a concentration gradient which increases from the outermost layer 16 to core 19, an increasing drug release rate may be achieved. In forming the rod implant 15 of FIG. 4., the multiple layers may be coextruded using well developed techniques. If desired, the concentration gradient profile from the rod center to its external surface may be smoothed by annealing the extrudate at a temperature slightly below the melt temperature of the copolymer matrix material so that thermal diffusion of the drug is effected. An alternative procedure for forming the multilayered depot of FIG. 4 with a drug concentration gradient is to form a core and coat it with successive layers of a copolymer solution containing the drug dissolved or dispersed therein. It is, of course, also within the scope of this invention to form a multilayered depot such as 15 of FIG. 4 by a combination of techniques, e.g., extrusion and coating; and to make multilayered depots wherein the drug concentration as well as the ratio of glutamic acid to ethyl glutamate in the copolymer differs from layer to layer. Varying the drug concentrations and the copolymer constituent ratio provides a means for varying the drug release rate from layer to layer.

Under some circumstances, it may be desirable to release two different substances in series. For example, in the depot 20 of FIG. 5., the outer layer 21 may contain a first chemotherapeutic drug which is to be delivered up to its toxic level and core 22 may contain a second chemotherapeutic drug which is then delivered subsequent to the attainment of the toxic level of the first drug. Likewise, the depot of FIG. 5 may be formed to contain in outer layer 21 a diagnostic agent which, when released through action of a pathologically-developed enzyme, will indicate an abnormal situation and then after giving such warning will release one or more drugs from core 22. The depot embodiments of FIGS. 4 and 5 may also be used to release more toxic drugs or more toxic dosages if the system does not respond to the first drug or dosage released. The rod embodiments of FIGS. 2, 4 and 5 may be sealed on their ends as described for the capsule of FIG. 6.

In constructing rod-configured depots, it may be desirable to postreat the rod surface to reduce the induction period required for the implanted depot to reach a steady-state drug release rate. Such postreating may be accomplished by soaking the depots in ethanol or water.

Figure 6:
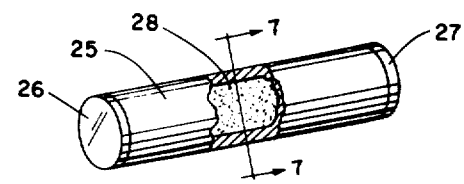
FIG. 6 illustrates a drug depot in the general form of a rod which is in essence a capsule comprising a closed tube containing all, or most, of the drug within the capsule.
Figure 7:
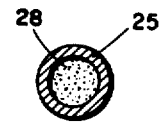
FIG. 7 is a transverse cross section of the capsule of FIG. 6 taken through plane 7—7 of FIG. 6.

FIGS. 6 and 7 illustrate another modification of a cylindrically configured depot constructed in accordance with this invention. This modification is a capsule in the form of a closed tube and it comprises a cylindrical casing 25 formed of the poly(glutamic acid-co-ethyl acrylate). Casing 25 is sealed at both ends, for example by end caps 26 and 27 also formed of the copolymer. Within the capsule there is a core 28 which may consist of only the drug or drugs to be delivered. Such an arrangement permits high drug loading and provides for the possibility of relatively high drug release rates. Alternatively, core 28 may be formed of the drug or drugs distributed throughout a matrix of the copolymer of a suitable glutamic acid/ethyl glutamate ratio, the drug loading in core 28 generally being relatively high compared to a rod form of the depot as shown, for example, in FIG. 2. Thus, the capsule form of depot, in conjunction with the various rod forms, provides for the attainment of a wide range of depot performance characteristics.

The capsule modification of the depot may be formed by any one of a number of suitable techniques. For example, if the core is made up of a drug only, the capsule casing may be fabricated, filled with drug and then capped. Alternatively, the drug core may be formed and then coated with a polymer solution by spraying, dipping, and the like. If the core is formed of the drug in a copolymer matrix, the components may be blended and shaped as previously described. Such a core may be inserted into a suitably-sized preformed casing which is then capped, or it may be coated with a copolymer solution. The core and capsule casing may also be coextruded, cut into desired lengths and then capped. Thus, this form of depot device lends itself to a wide variety of manufacturing techniques, all within well-developed skills.

When a capsule depot is constructed by inserting a drug core into a preformed casing, it may be desirable to prefill the casing with a suspending agent to ensure initial drug-casing contact and hence a rapid attainment of the desired drug release rate. This pretreatment ensures contact between the core and casing and thus in effect eliminates waiting for body fluid to enter the capsule to set up the condition necessary for the drug to permeate through the capsule walls. Among the liquids which may be used as suspending agents are physiologically acceptable oils, e.g., sesame oil, water and physiologically-balanced saline solutions.

Although the poly(glutamic acid-co-ethyl glutamate) used to form the casing around the core will normally have the same glutamic acid to ethyl glutamate ratio as that used as the matrix for the core, this is not necessary; and in some instances the use of two different copolymers may be desirable to obtain an even more exacting control over drug delivery.

The capsule modification of the cylindrically-configured depot constructed in accordance with this invention has several advantages in the administration of drugs, the release rate of which is to be relatively high, e.g., of the order of 50 $\mu$g/hour. One very important advantage is the possibility of attaining drug loadings as high as 80% to 98% by weight thus allowing a minimum overall size of depot and requiring a minimum amount of copolymer to be eventually removed by biodegradation. Another advantage lies in the fact that depots in the form of a capsule may more readily exhibit a constant rate of drug release to achieve maximum utilization of the drug payload.

Figure 8:
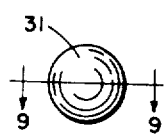
FIG. 8 shows a microcapsule spherical depot constructed in accordance with this invention.
Figure 9:
FIG. 9 is a cross section through the microcapsule of FIG. 8 taken through plane 9—9 of FIG. 8.

FIGS. 8 and 9 illustrate yet another configuration which the drug depot of this invention may assume, namely as a microcapsule. The microcapsule 30 has an outer coating 31 of only copolymer and a spherical (or other similar configuration) core 32 formed, as in the case of the closed tubing of FIGS. 6 and 7, of either pure drug or of a drug/copolymer blend.

The use of these microcapsule implants provides one way to deliver a mixture of drugs, some implants containing one drug and some another. Any suitable technique (tumbling, dipping, spraying, coacervation or the like) may be used to form such microcapsule implant devices.

The implant devices of this invention may be located in or near an organ of the body, or they may be implanted subdermally, e.g., in the forearm or sublingually. They may also be administered as uterine or vaginal inserts.

As previously noted, one factor influencing both the rate of drug release and rate of biodegradation of the depot is the synthesis of the copolymer, and in particular the manner in which debenzylation of the intermediate copolymer is effected. The preparation of the poly(glutamic acid-co-ethyl glutamate) is carried out in three stages: (1) synthesis and purification of the monomers, (2) polymerization and recovery of the benzyl-blocked intermediate, and (3) debenzylation of the intermediate and ether extraction of the copolymer product. The monomer synthesis begins with the N-carboxyanhydrides of benzyl glutamate and ethyl glutamate which are prepared by reaction of the esters with phosgene (added as a stock solution in benzene) using freshly distilled THF as solvent. The products are recovered by precipitation with petroleum ether and subsequently recrystallized from chloroform according to known procedures. The benzyl glutamate reaction takes approximately one hour at room temperature while the ethyl glutamate reaction requires approximately three hours.

Polymerization of the benzyl glutamate/ethyl glutamate copolymers is carried out at 25° C. in a 50/50 mixture of toluene/methylene chloride solvent. This solvent system appears to minimize differences in the reactivities of the monomers so that a uniform distribution of amino acids may be produced in the polymer. In an examplary reaction, 10 mole % benzyl glutamate N-carboxyanhydride and 90 mole % ethyl glutamate N-carboxyanhydride are added to a vacuum-dried reaction flask and further dried by cycling between vacuum and nitrogen purges. Freshly distilled solvent is added in amounts sufficient to achieve about 3% final polymer concentration. Triethylamine (1.31 M in benzene) is used as an initiator at a level of 2 mole % based on monomers. The reaction mixture is stirred under $N_2$ in a 25° C. constant temperature bath for 3 days. The product copolymer is then isolated by precipitation into methanol. NMR analyses of the benzyl glutamate/ethyl glutamate copolymer prepared by this technique indicate that the product copolymers have similar molar contents of monomer units as the starting mixtures of monomers. The procedure is, therefore, effective in providing good control over product composition during the polymerization step. Viscometric estimation of the molecular weights of these polymers indicate values of 105,000-160,000 (relative to viscosity correlations for polybenzyl glutamate). Thus, the benzyl-blocked copolymers can be prepared reproducibly in the same average molecular weight range, using this procedure. However, copolymers within a molecular weight range of between about 80,000 and 500,000 may be used. Those copolymers with molecular weights much below 80,000 are in general too brittle; while those having molecular weights above about 500,000 exhibit solution viscosities too high for casting purposes.

The benzyl-blocked copolymers are then converted to the final glutamic acid/ethyl glutamate copolymer by a debenzylation procedure which involves reaction with HBr under anhydrous conditions. Debenzylation is preferably carried out by dissolving the polymeric intermediate in freshly distilled benzene and bubbling HBr through the solution until the polymer precipitates. The reactor is then sealed and allowed to remain at 20°-25° C. for about 16 hours. A nitrogen purge is used to strip out HBr (which is typically present at greater than 15 times excess on a mole basis). The copolymer is then recovered by filtration, extracted for 24 hours with ether in Soxhlet apparatus, and vacuum dried at about 55° C.

The HBr concentration in the debenzylating step can be used to control the final copolymer composition, even though a large molar excess of HBr is used and its concentration does not significantly change during reaction. For example, if the HBr concentration is 0.07 g/ml, the final composition of the copolymer is 29/71; whereas when the HBr concentration is 0.05 g/ml, the composition is 26/74. In the selective debenzylation of the benzyl glutamate portion of the intermediate some de-ethylation will always occur. However, it is possible to obtain the desired final copolymer composition by beginning with the appropriate intermediate. For example, 15/85 benzyl glutamate/ethyl glutamate can be deesterified (at an HBr concentration of 0.05 g/ml for 12 hours) to a 20/80 glutamic acid/ethyl glutamate product containing a residual benzyl content of 0.68 mole %. In contrast, a 10/90 intermediate can be treated with 0.05 g/ml HBr for 24 hours to yield 20/80 glutamic acid/ethyl glutamate with an approximate residual of 0.03 mole % benzyl.

Drug depots prepared in accordance with this invention using the 20/80 poly(glutamic acid-co-ethyl glutamate) copolymer formed from the 15/85 benzyl glutamate/ethyl glutamate intermediate exhibit more rapid drug release rates and faster biodegradation than depots prepared from the 20/80 copolymer formed from the 10/90 benzyl glutamate/ethyl glutamate intermediate. It seems reasonable to postulate that the greater the degree of de-ethylation which must be effected to obtain the desired amount of glutamic acid, the greater is the amount of $\beta$-conformation of the copolymer. There is therefore provided, through the synthesis of the poly(glutamic acid-co-ethyl glutamate) copolymer, an added technique for controlling the rates of drug release and of biodegradation.

In forming the capsules for the following examples, a glass mandrel of a suitable diameter is dipped in and out of a solution of the copolymer, using, for example, dimethyl formamide, tetrahydrofuran or mixtures of these as the solvent. The coating solutions are preferably formed to have a solids concentration of between about 2% and about 5%. If desired, the glass mandrel may be coated with a release agent, e.g., stearic acid, before dipping is begun.

The dip-coating process of making capsules is carried out using a temperature-controlled solution, e.g., at 30° C. In order to obtain more acceptable reproducibilty in size, including wall thickness and integrity of the capsules, automatic cycle timers and counters are used to control the mandrel dipping and capsule sealing operations. Although oven-drying may be used, it is preferable to use a heat blower gun in connection with the dipping apparatus to dry the coated material for a precisely controlled time, e.g., 2 minutes, following each dip. After the desired coating thickness has been built up, the glass mandrel with the copolymer coating is dried in an oven at about 70° C. for a sufficient time to remove residual solvent, e.g., for about 24 hours. The mandrel with its coating is then placed in a distilled water bath for a time, e.g., about 24 hours, sufficient to swell the tubing so that it may be slipped off the mandrel. The resulting closed end tubing after being dried is ready for insertion of the drug core.

Caps for closing the one open end of the tubing formed are built up in the same manner on glass mandrels having diameters slightly larger than the diameter of the capsule tubing to allow the caps to be slipped over the open end.

Capsule wall thicknesses ranging between about 0.0025 cm and 0.025 cm may be built up in this manner.

The core may be formed with or without poly(glutamic acid-co-ethyl glutamate). If copolymer is added to the drug to form the core, then it is made by extrusion as described above for making rod depots. If the core is formed of essentially all drug, then only enough solvent (usually from about 0.1% to about 5% by drug weight) is used to impart to the drug particles a slight tendency to cohere prior to extrusion. This may conveniently be accomplished by adding an excess of solvent and then permitting it to evaporate until the desired amount remains. There should be essentially no liquid to express from the drug as it is extruded under a suitable pressure, e.g., about 10,000 psi.

As previously noted, in order to ensure that a saturated solution of the drug completely fills the interior of the capsule and makes contact with the tube walls, the capsule tubing may be partially filled with a suspending agent, e.g., sesame oil, a physiologically-balanced saline solution, or water with or without a minor amount of methyl cellulose as a thickening agent. In some cases it is difficult to maintain liquid around the drug core when heat is applied to drive off the solvent of the cement used to seal the capsules. This difficulty may be overcome by adding a few small NaCl crystals (about 0.2 to about 1 mg) to the capsule prior to sealing and allowing osmotic forces to fill the capsule with liquid after implantation. Typically, capsules 2 cm in length, with 0.19 cm inside diameter and 0.16 cm wall thicknesses filled with water within five days when implanted subcutaneously in mice or immersed in physiological saline solution at 37° C. Similar tubes which were exposed to steam at 15 psig, 121° C., became filled in approximately two hours.

Alternatively to the filling of the capsule tube with a suspending agent and to the use of a small amount of solvent to form an extrudable drug core, the suspending agent may be added to the drug before extruding and used to adhere the drug particles while remaining in the core as a suspending liquid. Thus, a small amount of sesame oil may be added to the drug prior to forming it into the core.

The dried, closed-end capsule tubing and cap tubing are cut to the desired lengths. The drug core is cut to the desired length, inserted into the capsule tubing, and the cap is placed in position. The capped end of the capsule is then dipped several times into the solution of copolymer to cement and seal the cap to the capsule. The capsule depot formed is then dried at about 70° C. to remove all solvent, e.g., for about 24 hours.

The drug depot, the process for its preparation, and the process for its use to attain a continuous sustained drug release are further described in the following examples which are meant to be illustrative and not limiting.

EXAMPLE 1

Depots of naltrexone, a narcotic antagonist, were made in capsule form by the above procedure and evaluated for in vitro and in vivo release of the drug. A 22/78 glutamic acid/ethyl glutamate copolymer was prepared by the above detailed procedure, the intermediate debenzylated to form the copolymer being a 10/90 benzyl glutamate/ethyl glutamate copolymer. The drug cores were essentially pure naltrexone labelled with $^{14}C$.

The capsules were formed by dipping a glass mandrel of 0.069-inch (0.175-cm) diameter into a 5% dimethyl formamide solution of the polymer to form a wall thickness of 0.0038 cm (0.0015 inch). The completed capsules, formed in the manner described, had a diameter of 0.18 cm (0.0709 inch). They were cut to lengths of 1 and 2 cms.

Figure 10:
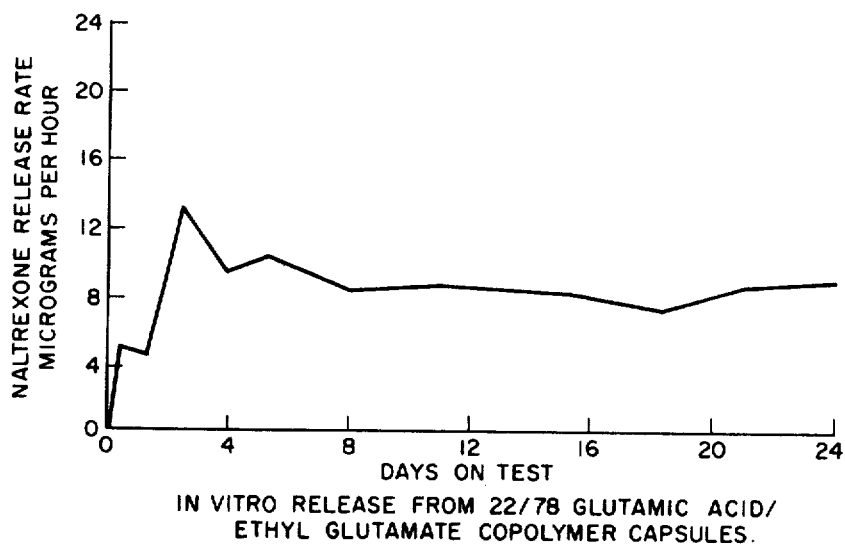
FIG. 10 is a plot of the in vitro release of naltrexone from 22/78 glutamic acid/ethyl glutamate copolymer capsules as a function of time.

Two of the one-centimeter capsules, each having a naltrexone content of 21.1 mg were evaluated for their in vitro release of the drug. In making these in vitro evaluations the capsules were rinsed briefly with Earle's Balanced Salt Solution and then placed in separate stoppered test tubes containing 10 ml of the Earle's solution. The tubes were placed in a shaker water bath at 37° C. and were gently agitated. Drug concentration of the solution was periodically assayed by scintillation counting techniques to permit an evaluation of the in vitro drug-release behavior of the copolymers. (The solutions were replaced sufficiently frequently that the naltrexone concentration remained far below saturation, i.e., below ~460 mg/100 ml). The average drug release rate for these two capsules is plotted as a function of time in FIG. 10. It will be seen that the depots rapidly attained a steady-state release rate of 3-10 $\mu$g/hour. At the end of the 24 days, they had released about one-third of their initial drug load.

Figure 11:
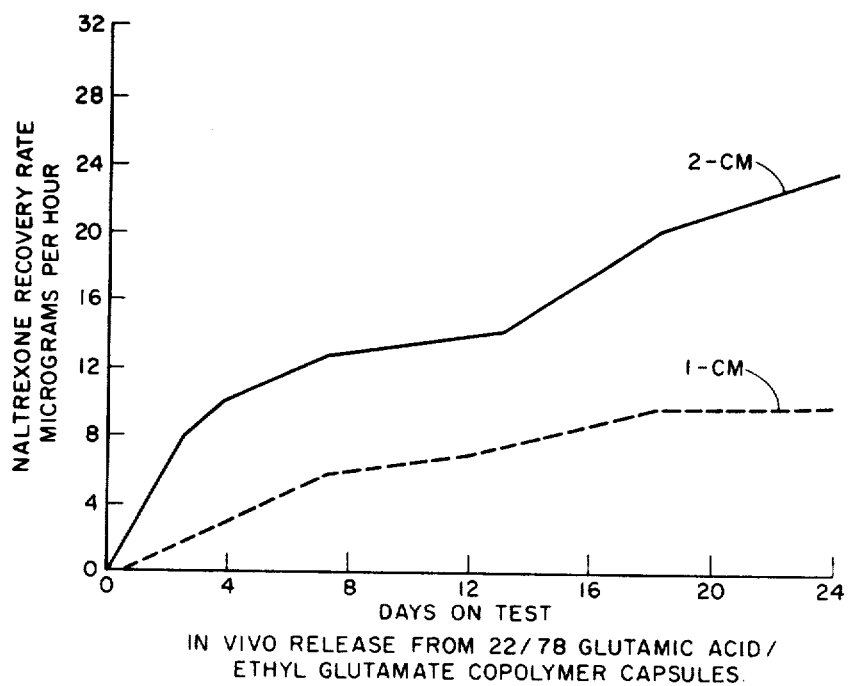
FIG. 11 is a plot of the in vivo release of naltrexone from 22/78 glutamic acid/ethyl glutamate copolymer capsules as a function of time.

Three one-centimeter and two two-centimeter capsule depots were evaluated for in vivo release of the drug. In making these evaluation, implants were introduced in mice and urinary radioactivity was determined as a measurement of drug release. The average release rates over a span of about 24 days for the depots of these two lengths are plotted in FIG. 11. It will be seen that a plateau of about 8 $\mu$g/hour was eventually attained in the one-centimeter depots in vivo, a rate which was comparable to the release rate in vitro. However, the attainment of this plateau required a somewhat longer time. The two-centimeter depots released naltrexone at slightly more than double the rate of the shorter devices. A release rate of about 24 $\mu$g/hour of this drug is considered to be within a practical delivery rate range.

EXAMPLE 2

A number of capsules were prepared using the preferred method described, i.e., heat blowing to dry after each succeeding dip and automatic timers to control alternating times of dipping and withdrawing.

Copolymers of glutamic acid/ethyl glutamate having molar ratios of 30/70, 20/80, 18/82 and 13/87 were formulated for the core materials and the cores were extruded from a stiff paste composed of $^3$H-labeled naltrexone base using sesame oil as an extrusion aid. Some capsules were filled with additional sesame oil in order to investigate the value of maintaining an oil-filled reservoir.

The capsules were implanted subcutaneously in mice, and the urine was monitored for radioactivity using liquid scintillation counting procedures. The release rates were calculated by assuming that 65% of the naltrexone released from the capsules appeared in the urine (as parent compound and metabolites). This fractional recovery was established in separate experiments wherein mice were administered subcutaneous injections of radioactive naltrexone and then studied to determine urinary and fecal distribution of radioactivity. In addition, the area under the release rate vs. time curves were routinely measured to determine if the total drug recovered was equivalent to the initial drug contained in the capsules.

30/70 Glutamic acid/ethyl glutamate copolymer

Figure 12:
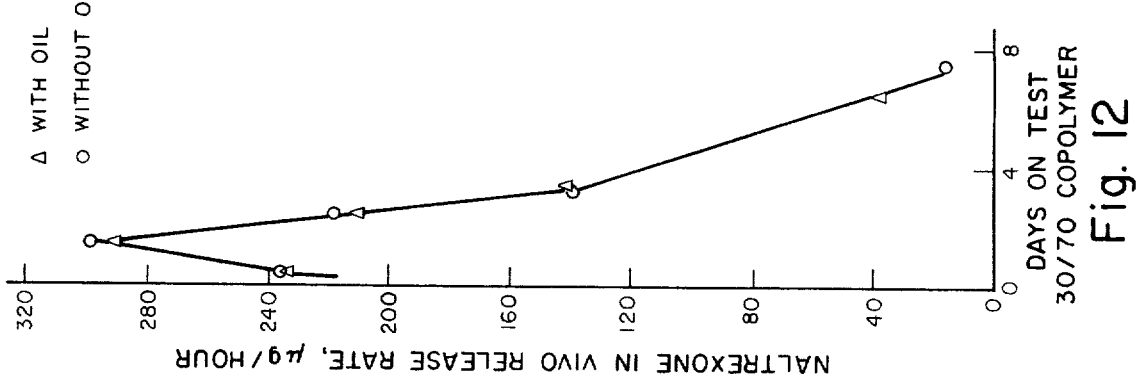
FIG. 12 is a plot of the in vivo release of naltrexone from 30/70 glutamic acid/ethyl glutamate copolymer capsules as a function of time.

FIG. 12 shows the release rates for capsules 1.5 cm in length, 0.18 cm in inside diameter, and 0.004 to 0.005 cm in wall thickness. These were filled with 40 mg cores composed of 22 mg naltrexone and 18 mg sesame oil (all the oil was absorbed in the core). Additional sesame oil was added to some of the capsules. However, in these capsules release rates were sufficiently rapid to essentially nullify any effect of the added oil. In both cases the rates were extremely rapid, peaking at approximately 300 µg/hour and then dropping off within eight days. The results were in close agreement with rates predicted on the basis of the measured permeability of films of the copolymer.

Capsules such as these are suitable for delivering large bursts of drugs over a short period of time.

20/80 Glutamic acid/ethyl glutamate copolymer

Figure 13:
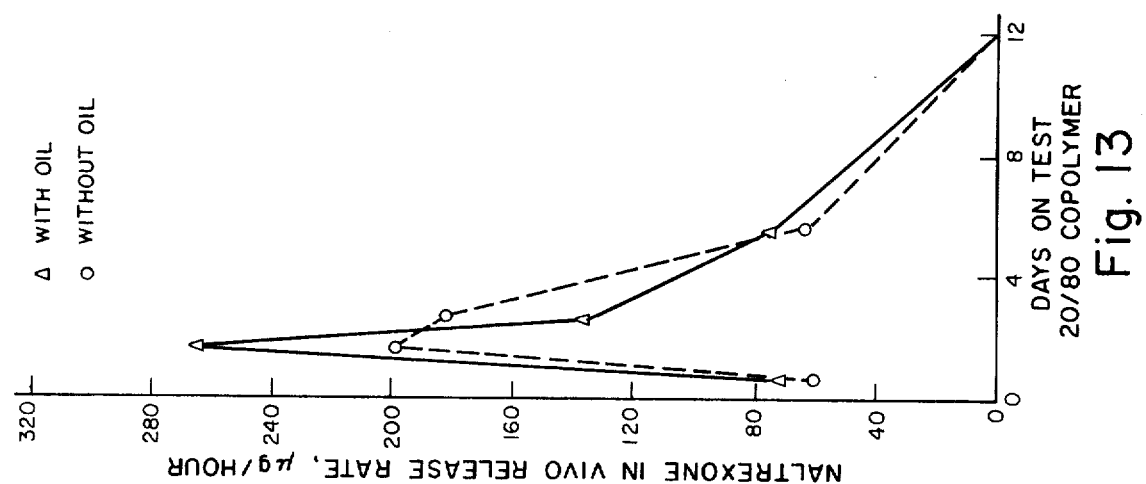

Capsules were prepared 1 cm in length, 0.18 cm in inside diameter, 0.005 cm in wall thickness, and they were filled with pure naltrexone rods weighing 22 mg. Sesame oil was added to some of the tubes, while others were left free of oil to provide a basis for comparison. The release rates are shown in FIG. 13. Capsules with oil exhibited slightly higher rates, peaking at 260 µg/hr and then rapidly falling off. Capsules without oil peaked at 200 µg/day, but they, too, were exhausted of drug within 12 days.

Figure 14:
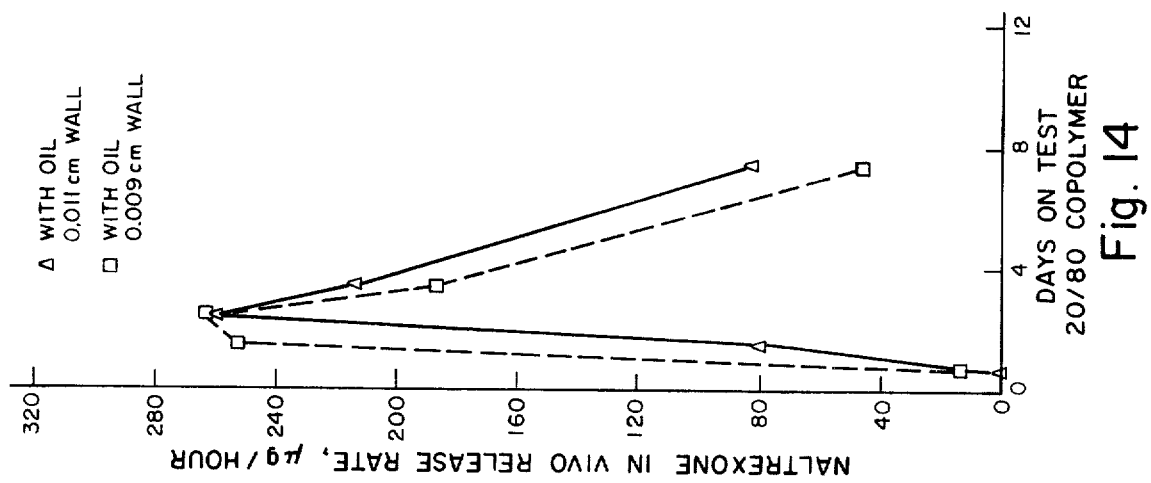
FIGS. 13 and 14 are plots of the in vivo release of naltrexone from 20/80 glutamic acid/ethyl glutamate copolymer capsules as a function of time.

A second set of capsules was prepared in order to study the influence of wall thickness and sesame oil. These capsules were longer than those above, 1.5 cm, and they were either 0.009 cm or 0.011 cm in wall thickness. They were filled with 40 mg rods composed of 22 mg naltrexone and 18 mg sesame oil. Additional oil was added to fill the tubes. As is shown in FIG. 14, there was little difference that could be ascribed to wall thickness; and the magnitude of release was similar to that shown in FIG. 13. The larger surface of the 1.5 cm capsules apparently compensated for their thicker walls.

18/82 Glutamic acid/ethyl glutamate copolymer

The release rates from these capsules, 1 cm in length, 0.005 cm in wall thickness, and filled with 24 mg rods (composed of 16 mg naltrexone and 8 mg of sesame oil) are shown in FIG. 15. The rate gradually rose over the first 3 days to a range of 20 to 40 µg/hr, which was maintained for approximately 18 days. During this interval approximately 13 mg was administered out of the initial 16 mg loading of naltrexone. The remaining 3 mg was released over the next 12 days.

The release behavior of these capsules was quite unlike that of the 20/80 capsules discussed above, despite the small difference in copolymer composition. However, the moisture absorption results (80% for the 18/82 copolymer and 175% for the 20/80) appeared to provide an indication of the real differences between the copolymers, and hence offers a way to characterize the capsule materials.

No residues of the capsule materials were found 90 days after implantation, showing that they possessed the requisite biodegradability.

13/87 Glutamic acid/ethyl glutamate copolymer

Capsules 1 cm in length and 0.008 cm in wall thickness were fabricated from the 13/87 copolymer. These were filled with 22 mg rods that contained 12 mg of naltrexone and 10 mg of sesame oil. FIG. 16 shows that the release rate was quite slow, peaking at approximately 8 µg/hr by day 56, and it was prolonged for almost 100 days. Residues of this slowly degrading copolymer were still evident at the implant sites 180 days after implantation.

From these data for capsules formed from four different copolymer compositions it will be seen that the smaller the molar ratio of glutamic acid to ethyl glutamate, the lower is the peak delivery rate at which the drug is released and the longer is the time over which drug is released.

EXAMPLE 3

Rod-configured depots were fabricated by extruding a stiff paste composed of 45% copolymer, 45% drug, and 10% tetrahydrofuran. A simple compression mold fitted with a die was used as the extruder. The rods, after they were dried at 70° C. for 5 days to remove the solvent, were 0.23 cm in diameter, 1 cm in length and contained 50% of the drug by weight. The copolymer was 20/80 poly(glutamic acid-co-ethyl glutamate) and it was prepared by partial de-esterification of 15/85 benzyl glutamate/ethyl glutamate intermediate. The drugs were $^{14}$C-labeled progesterone and norethisterone. Twelve implants were made for each drug. In order to eliminate or control the initial burst of drug release, eight implants of each group of twelve were pretreated, while the remaining four received no pretreatment to serve as controls. In the case of the progesterone-containing implants, the pretreatment was a one-hour soak in 50% ethanol or in sterile water; and in the case of the norethisterone-containing implants, it was a one-half hour or one-hour soak in 50% ethanol.

The depots were implanted subcutaneously in mice, and the urinary and fecal recovery of radioactivity was measured. The data obtained for the depots containing progesterone are plotted in FIG. 17 as the release rate in micrograms per day as a function of time. In determining the release rate of progesterone, the excreta data were divided by 0.8 in order to compensate for the fact that a small portion of the radioactive $^{14}$C was found to be present in the expired air. The data for the norethisterone implants are plotted in FIG. 18 as drug recovery rates as a function of time. In this case the urinary and fecal data were not corrected.

Figure 17:
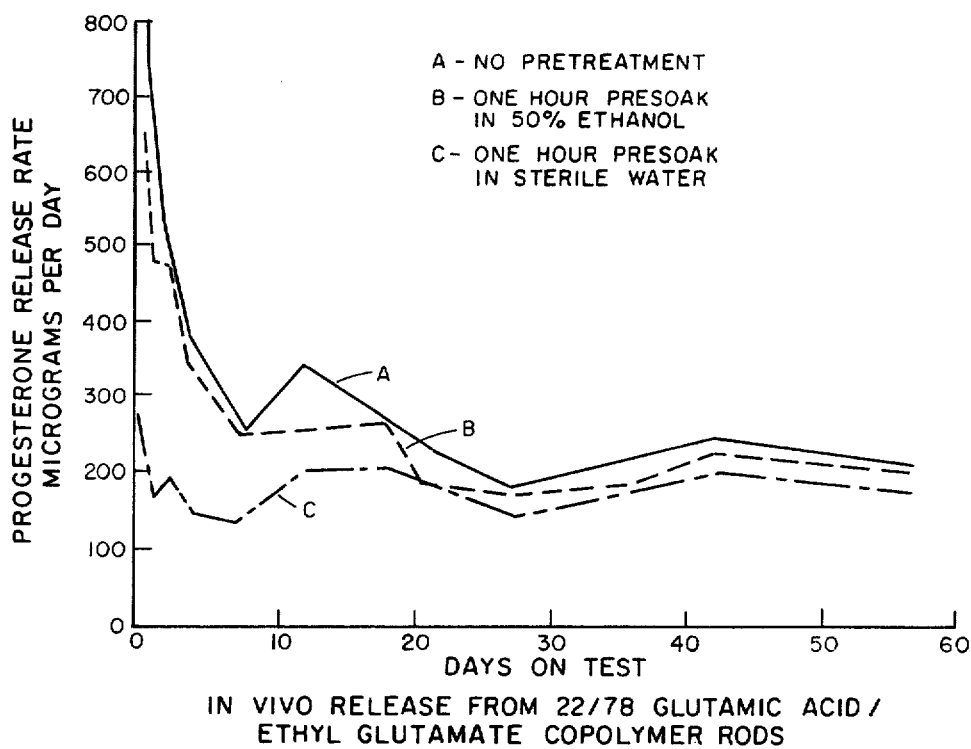
FIG. 17 is a plot of the in vivo release of progesterone as a function of time from 22/78 glutamic acid/ethyl glutamate copolymer rods with and without pretreatment to control the initial burst of drug release.

Although FIG. 17 shows a relatively continuous release rate of about 200 µg/day for the progesterone-containing rods for about 56 days, these rods remained on test and continued to deliver this drug at substantially this same rate for some 115 days. The drug was essentially exhausted after about 160 days.

Figure 18:
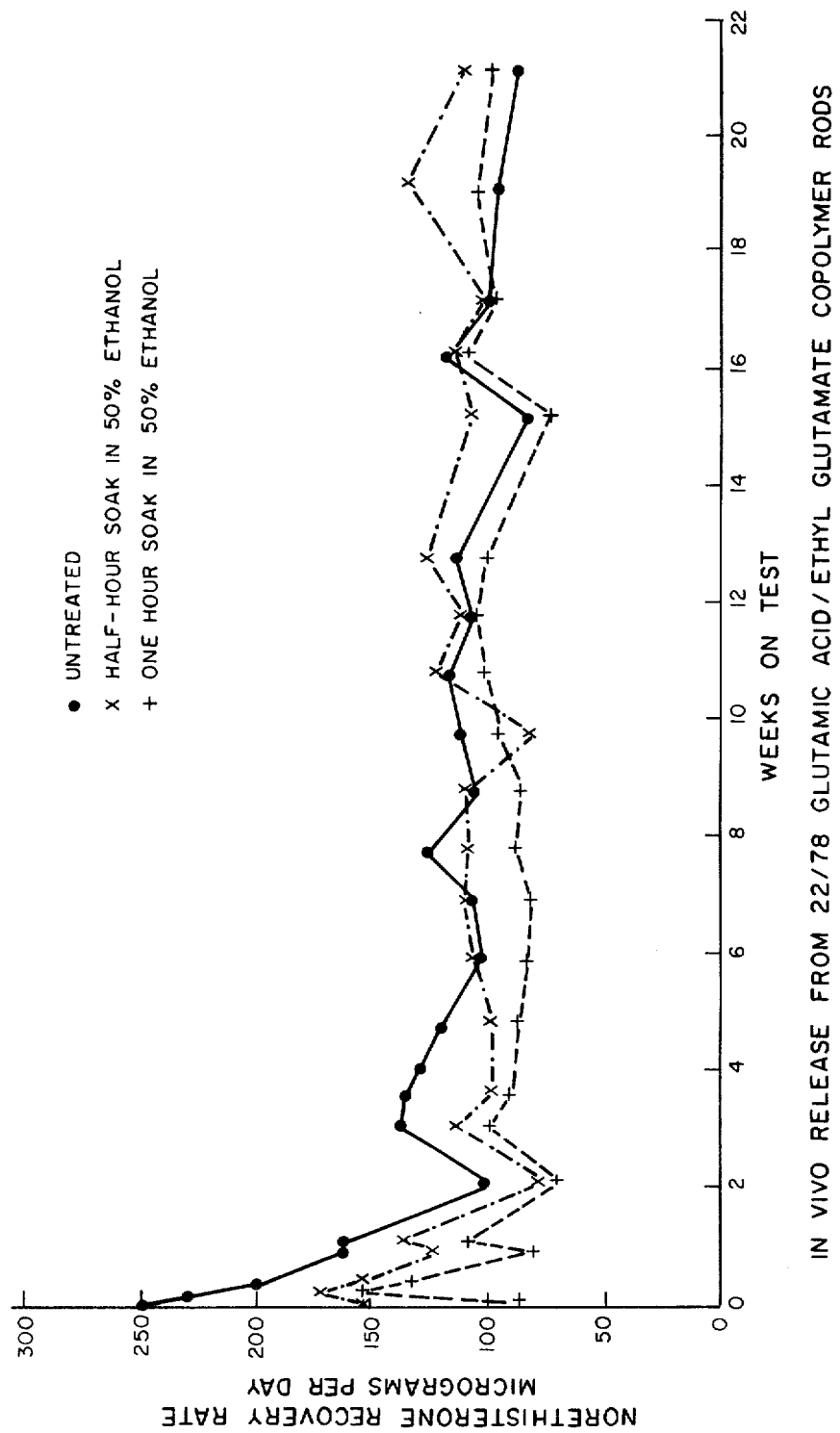
FIG. 18 is a plot of the in vivo release of norethisterone as a function of time from 22/78 glutamic acid/ethyl glutamate copolymer rods with and without pretreatment to control the initial burst of drug release.

FIG. 18 shows that the recovery rate for the norethisterone rods were maintained at about 70 µg/day over some 21 weeks, at which time the rate was still holding essentially constant. In both of these depot systems, the pretreatment soaks in 50% ethanol or water were effective in reducing or essentially eliminating the initial drug bursts.

EXAMPLE 4

Figure 19:
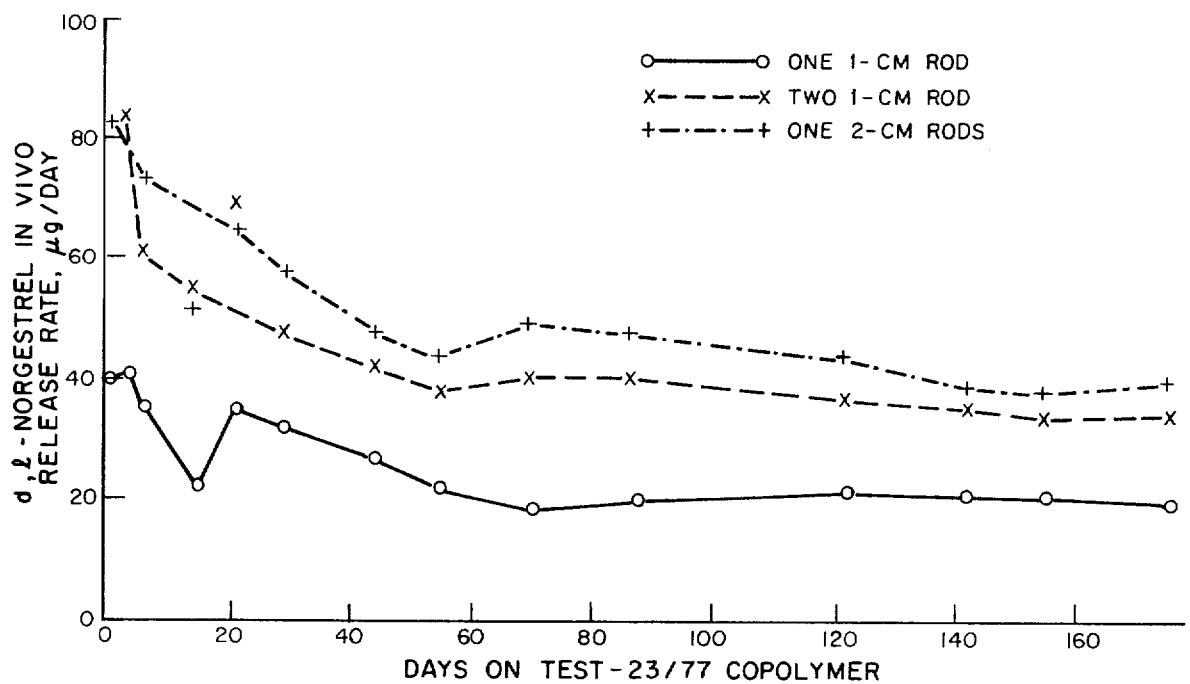
FIG. 19 is a plot of the in vivo release of norgestrel as a function of time from 23/77 glutamic acid/ethyl glutamate copolymer rods.

Rod-configured depots were prepared as described in Example 3. The copolymer was 23/77 poly(glutamic acid-co-ethyl glutamate), d, l-nogestrel ($^{14}$C-labeled) was used as the drug and the rods were 0.12 cm in diameter. Rods cut to 1 cm and 2 cm lengths were implanted subcutaneously in mice, and the urine and feces were monitored for radioactivity. FIG. 19 shows the results. The release rate appears to be directly proportional to the length (surface area) of the rods.

EXAMPLE 5

The permeabilities of 7/93 and 13/87 poly(glutamic acid-co-ethyl glutamate) were measured using $^{14}$C-labelled d, l-norgestrel (at 54 DPM/$\mu$g) and progesterone (at 22 DPM/$\mu$g) and from these data it was possible to predict the release rate from a capsule containing these drugs. The copolymers were prepared as previously described, using a 5/95 intermediate of benzyl glutamate/ethyl glutamate to make the 7/93 copolymer and a 10/90 intermediate to make the 13/87 copolymer.

Permeabilities were measured in a two-chambered glass cell which exposed one side of a 5.1 cm$^2$ test film to an aqueous solution saturated with the drug. The downstream chamber on the other side of the film contained 50 cm$^3$ of Earle's balanced salt solution. The cells were maintained at 37° C. and the permeant concentrations in the Earle's solution were determined by scintillation counting, the samples being taken at least once a day.

The measured permeabilities are given in Table 1 along with the predicted release rates from a capsule 1 cm long, 0.23 cm in diameter having a wall thickness of 0.0038 cm and a surface area of 0.92 cm$^2$.

From the data of Table 1 it will be seen that varying the copolymer composition provides a means to vary the permeability of the depot structure copolymer and hence of the drug release rate. The data also show that the permeability rates of different drugs differ for any one copolymer composition. There is thus provided an added degree of flexibility in designing a drug depot to attain a desired release rate. The combining of the drug and copolymer composition to achieve optimum results is within the skill of the art. In choosing an optimum release rate such factors as the total dose to be delivered, the duration of dose desired from any given depot, and the maximum size and number of depots implanted will be considered.

The depot matrix structure, e.g., rod, tube, capsule, sphere or chip, degrades through the action of body fluids thereon.

TABLE 1

DRUG PERMEABILITY THROUGH RIBBONS OF POLY(GLUTAMIC ACID-CO—ETHYL GLUTAMATE)

| Drug | Polymer Composition | Ribbon Thickness Mils | Days on Test | Permeability $\mu$g · mil hr · cm$^2$ | Predicted Capsule Release Rate $\mu$g/day |
|---|---|---|---|---|---|
| Progesterone | 7/93 | 1.5 | 1 | 0.9 | 13.4 |
| | | | 3 | 1.2 | 17.9 |
| | | | 7 | 1.6 | 23.8 |
| | | | 9 | 1.6 | 23.8 |
| | 13/87 | 1.0 | 3 | 0.86 | 12.8 |
| | | | 6 | 1.5 | 22.3 |

TABLE 1-continued

DRUG PERMEABILITY THROUGH RIBBONS OF POLY(GLUTAMIC ACID-CO—ETHYL GLUTAMATE)

| Drug | Polymer Composition | Ribbon Thickness Mils | Days on Test | Permeability $\mu$g · mil hr · cm$^2$ | Predicted Capsule Release Rate $\mu$g/day |
|---|---|---|---|---|---|
| | | 2.0 | 3 | 0.5 | 7.4 |
| | | | 6 | 1.5 | 22.3 |
| | | | 14 | 3.7 | 55.1 |
| | | | 15 | 3.4 | 50.6 |
| d,l-Norgestrel | 7/93 | 1.8 | 3 | 0.7 | 10.6 |
| | | | 9 | 0.7 | 10.6 |
| | 13/87 | 2.0 | 2 | 0.4 | 6.5 |
| | | | 9 | 0.34 | 5 |

Because of the chemical nature of the copolymer matrix material, it is believed that it is finally hydrolyzed to amino acids or to amino acid related materials. The rate of biodegradation is predetermined and controlled by the composition of the copolymer and its configuration, i.e., $\alpha$- or $\beta$-form or mixtures thereof. Thus, the greater the mole percent of glutamic acid, the more rapid is the rate of biodegradation; and the greater the amount of $\alpha$ form of the copolymer present, the more rapid is the biodegradation. In predetermining the rate of biodegradation for a depot, an important determining factor is the frequency with which the depot is to be replaced. For example, it is thought that a depot containing a fertility control drug should be capable of releasing the drug at an effective rate for a year, in which case, biodegradation of the depot matrix structure need not be completed before two years after implant. On the other hand, if it is necessary to implant a depot containing a narcotic antagonist every month, then the biodegradation rate of the depot matrix structure must be considerably more rapid so that large numbers of empty depots do not accumulate in the host.

The above-detailed description and examples illustrate the fact that the drug delivery depots of this invention offer a great range of flexibility in release rates, in total release periods, in the drugs which can be delivered and in biodegradation rates. These factors may be predetermined and realized through the choice of the poly(glutamic acid-co-ethyl glutamate) compositions used, of the configuration of the implant device and of the drug loading. The implants of this invention exhibit biocompatibility and biodegradability.

It will thus be seen that the objects set forth above, among those made apparent from the preceding description, are efficiently attained and, since certain changes may be made in carrying out the above method and in the article set forth above without departing from the scope of the invention, it is intended that all matter contained in the above description or shown in the accompanying drawings shall be interpreted as illustrative and not in a limiting sense.

I claim:

1. A depot suitable for implanting within a living host for the controllable release of at least one substance within said host, said depot not in the form of a film or suture, comprising a matrix structure containing said substance in releasable form said matrix being formed of a poly(glutamic acid-co-ethyl glutamate) in which the mole percent of glutamic acid ranges between about 5 and about 50 and having a viscosity average molecular weight of about 80,000 to about 500,000 and which is hydrophilic and of uniform composition throughout.

2. A depot in accordance with claim 1 wherein said structure is a cylindrical shape.

3. A depot in accordance with claim 2 wherein said substance amounts up to about 70% by weight of said depot.

4. A depot in accordance with claim 2 wherein the surface of said rod is treated to control the initial burst of substance release shortly after said depot is implanted within said living host.

5. A depot in accordance with claim 2 wherein the concentration of said substance is uniform throughout said rod.

6. A depot in accordance with claim 2 wherein the concentration of said substance varies throughout said rod.

7. A depot in accordance with claim 2 wherein said depot contains a plurality of said substances for release in sequence.

8. A depot in accordance with claim 1 wherein said cylindrical-shape is a sealed capsule comprising a casing and a core.

9. A depot in accordance with claim 8 wherein said substance amounts up to about 98% by weight of said depot.

10. A depot in accordance with claim 8 wherein said casing is formed only of said poly(glutamic acid-co-ethyl glutamate).

11. A depot in accordance with claim 8 wherein said core is formed of said substance.

12. A depot in accordance with claim 8 wherein said core is formed of said substance mixed with a minor proportion of said poly(glutamic acid-co-ethyl glutamate).

13. A depot in accordance with claim 8 wherein said capsule contains a suspending agent for ensuring contact between said core and the internal wall of said casing.

14. A depot in accordance with claim 13 wherein said suspending agent comprises water, a physiological saline solution, sesame oil or crystals of sodium chloride.

15. A depot in accordance with claim 8 wherein the external surface of said casing is treated to control the initial burst of substance release shortly after said depot is implanted with said living host.

16. A depot in accordance with claim 8 wherein said capsule is of a size to be implanted by trocar.

17. A depot in accordance with claim 1 wherein said poly(glutamic acid-co-ethyl glutamate) exhibits a moisture regain of at least 15% of its weight within 48 hours when immersed in a buffered physiological saline solution maintained at 37° C.

18. A depot in accordance with claim 1 wherein said poly(glutamic acid-co-ethyl glutamate) is formed of $\alpha$ and $\beta$ configurations, the ratio of $\alpha$ to $\beta$ being adjusted to realize a predetermined drug permeability rate and structure biodegradation rate.

19. A depot in accordance with claim 1 wherein said poly(glutamic acid-co-ethyl glutamate) has a molecular weight ranging between about 80,000 and 500,000.

20. A depot in accordance with claim 1 wherein said substance is a drug.

21. A depot in accordance with claim 21 wherein said drug is a fertility control agent.

22. A depot in accordance with claim 22 wherein said fertility control agent is a steroid.

23. A depot in accordance with claim 23 wherein said steroid is progesterone.

24. A depot in accordance with claim 22 wherein said steroid is d,l-norgestrel.

25. A depot in accordance with claim 22 wherein said steroid is levonorgestrel.

26. A depot in accordance with claim 22 wherein said steroid is norethisterone.

27. A depot in accordance with claim 20 wherein said drug is a narcotic antagonist.

28. An implant device in accordance with claim 27 wherein said narcotic antagonist is naltrexone.

* * * * *